United States Patent

Rossi, Jr. et al.

[11] Patent Number: 5,529,929
[45] Date of Patent: Jun. 25, 1996

[54] OPTICAL RESOLUTION OF ALKYL 1,4-BENZODIOXAN-2-CARBOXYLATES USING ESTERASE FROM SERRATIA MARCESCENS

[75] Inventors: Richard F. Rossi, Jr., Norton; Charles M. Zepp, Hardwick; Donald L. Heefner, Hudson, all of Mass.

[73] Assignee: SepraChem, Inc., Marlborough, Mass.

[21] Appl. No.: 477,381

[22] Filed: Jun. 7, 1995

[51] Int. Cl.$^6$ .................................................. C12P 41/00
[52] U.S. Cl. ........................... 435/280; 435/125; 435/881
[58] Field of Search ..................................... 435/280, 125, 435/881

[56] References Cited

U.S. PATENT DOCUMENTS

| | | | |
|---|---|---|---|
| 5,037,747 | 8/1991 | Coffen | 435/125 |
| 5,182,198 | 1/1993 | Kise et al. | 435/126 |
| 5,274,300 | 12/1993 | Dodds et al. | 435/280 |
| 5,371,014 | 12/1994 | Matsuyama et al. | 435/280 |
| 5,374,554 | 12/1994 | Komatsubara et al. | 435/252.3 |
| 5,378,627 | 1/1995 | Shibatani et al. | 435/280 |
| 5,393,664 | 2/1995 | Kira et al. | 435/156 |

FOREIGN PATENT DOCUMENTS

0343714A1  11/1989  European Pat. Off. .
0362556A1  11/1990  European Pat. Off. .

OTHER PUBLICATIONS

"Optimisation of Chiral Separation of Doxazosin Enantiomers . . .", Ley et al., *Recent Advances in Chiral Separations*, 97–103 (1991).

"Quantitative Analyses of Biochemical Kinetic Resolutions of Enantiomers", Chen et al., *J. Am. Chem. Soc.* 104, 7294–7299 (1982).

*Primary Examiner*—Michael G. Wityshyn
*Assistant Examiner*—S. Saucer
*Attorney, Agent, or Firm*—Heslin & Rothenberg

[57] ABSTRACT

A process for resolving racemic alkyl 1,4-benzodioxan-2-carboxylates useful as intermediates in the synthesis of optically pure pharmaceutical compounds such as (S)-doxazosin is disclosed. The process utilizes a microbial enzyme derived from *Serratia marcescens* to catalyze the enantioselective hydrolysis of the alkyl (S)-1,4-benzodioxan-2-carboxylate enantiomer of the racemic mixture to its corresponding carboxylic acid at a faster rate than the R-enantiomer. An enantiomerically pure S-configured carboxylic acid is thereby formed for subsequent pharmaceutical synthesis. The nonhydrolyzed alkyl (R)-1,4-benzodioxan-2-carboxylate enantiomer can also be isolated and racemized, and the enzymatic hydrolysis reaction repeated.

11 Claims, No Drawings

OPTICAL RESOLUTION OF ALKYL 1,4-BENZODIOXAN-2-CARBOXYLATES USING ESTERASE FROM SERRATIA MARCESCENS

The present invention relates to a process for the resolution of alkyl 1,4-benzodioxan-2-carboxylates having the general formula (I)

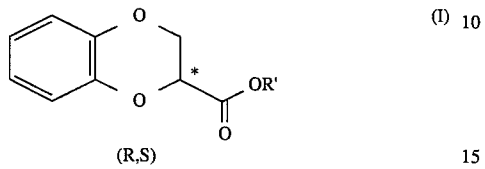

wherein R' represents an alkyl group, preferably ethyl. (Use of an asterisk (*) herein indicates the chiral center.) The invention also relates to the enantioselective hydrolysis of one enantiomer in the racemic mixture of such esters by use of a microbial esterase derived from *Serratia marcescens* to form an enantiomerically pure (S)-1,4-benzodioxan-2-carboxylic acid.

BACKGROUND OF THE INVENTION

Optically active esters such as alkyl 1,4-benzodioxan-2-carboxylates having a single chiral center adjacent to the carboxyl group have utility as precursors in the chemical synthesis of various pharmaceutical compounds. Resolution of the racemic ester mixtures into individual enantiomers provides a convenient point in the overall synthetic route to the corresponding optically pure pharmaceutical compound.

For example, doxazosin is an optically active pharmaceutical compound useful in the treatment of patients with hypertension, benign prostatic hyperplasia (BPH) and, perhaps, in the treatment of patients with elevated serum low density lipoprotein (LDL) levels. Doxazosin has the chemical structure (II)

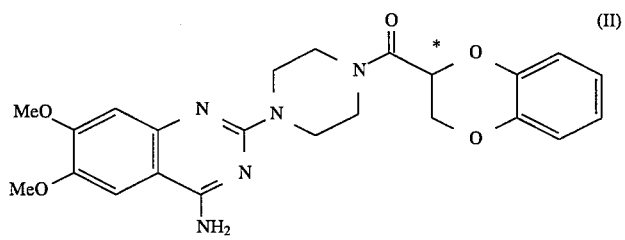

More specifically, doxazosin, the chemical name of which is 4-amino-2-[4-(1,4-benzodioxan-2-carbonyl)piperazin-1-yl]-6,7-dimethoxyquinazoline also known as 1-(4-amino-6,7-dimethoxy-2 -quinazolinyl)-4-[(2,3-dihydro-1,4-benzodioxan-2-yl)carbonyl] piperazine, is a quinazoline derivative having a single chiral center located on the carbon adjacent to the carboxyl group. This gives rise to a pair of enantiomers. However, doxazosin is currently commercially available only as the racemic mixture. However, it appears that administration of the optically pure (S)-(+)- enantiomer of doxazosin may provide the advantages associated with the administration of the racemic mixture without the accompanying adverse side effects. (See PCT application WO 94/09785). Isolation of the two enantiomers of doxazosin is therefore desirable.

Doxazosin has been resolved into its enantiomers on an analytical scale by Ley et al. See *Recent Advances in Chiral Separations*, Steven and Wilson Editors, Plenum Press, New York (1991) pages 97–103. However, there are no reports in the literature of a preparative-scale separation of the enantiomers. Thus, a need exists for a convenient and economic method for producing the enantiomers of racemic doxazosin which can be performed on a commercial scale.

The synthesis of doxazosin includes, as an intermediate step, the reaction of its optically active chemical precursor, ethyl 1,4-benzodioxan-2-carboxylate having the formula (III).

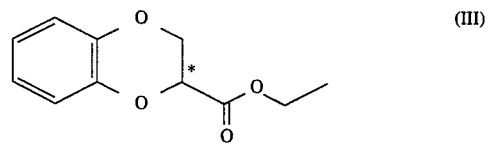

Ethyl 1,4-benzodioxan-2-carboxylate has a chiral center adjacent to the carbonyl. Thus, resolution of the racemic mixture of this doxazosin precursor into isolated enantiomers would permit large-scale syntheses of the individual enantiomers of doxazosin. In particular, resolution of the ethyl (S)-1,4-benzodioxan- 2-carboxylate or (S)-1,4-benzodioxan-2-carboxylic acid precursor would allow synthesis of the preferred S-enantiomer of doxazosin at a commercial level.

Resolution of racemic mixtures of chiral compounds can often be achieved by subjecting the mixture to the stereoselective action of various enzymes. Generally, enzymes for use in resolutions should exhibit a high degree of stereoselectivity for catalyzing the reaction of one isomer to the exclusion of others. For example, enzymatic resolution by enantioselective hydrolysis of various ester compounds has been widely employed for the lab-scale, preparative-scale, and industrial-scale production of many optically pure acids and esters.

One class of enzymes, the hydrolases, which includes lipases, proteases, esterases, trypsins, chymotrypsins, and dextranases, for example, is often used in the resolution of enantiomers because they are commercially available at reasonable cost, they do not require expensive cofactors, and some exhibit reasonable tolerance to organic solvents. Additionally, hydrolases are known to stereoselectively catalyze the hydrolysis of certain carboxylic acid derivatives, including esters.

However, resolution of the enantiomers of alkyl 1,4-benzodioxan-2-carboxylates by stereoselective enzymatic hydrolysis has not heretofore been described. Such a resolution is desirable in order to provide optically pure alkyl 1,4-benzodioxan-2-carboxylates and corresponding acids for use as synthetic precursors in the manufacture of pharmaceutical compounds, such as (S)-doxazosin.

Therefore, a need exists for an inexpensive and efficient method for producing on a commercial scale the individual enantiomers of alkyl 1,4-benzodioxan 2-carboxylates.

SUMMARY OF THE INVENTION

As a result of various studies, it has now been unexpectedly found that optically pure alkyl 1,4-benzodioxan- 2-carboxylates can be conveniently prepared in high enantiomeric purity by esterase catalyzed hydrolysis of the corresponding racemic ester compound. The resolution process of the present invention is accomplished through the use of a microbial esterase derived from *Serratia marcescens* that stereoselectively catalyzes hydrolysis of the S-ester at a faster rate than the R-ester. Optically pure (S)-1,4-benzodioxan-2-carboxylic acid is produced while the corresponding alkyl (R)-1,4-benzodioxan- 2-carboxylate enantiomer remains as the ester. Alkyl as used herein refers to linear, branched and cyclic hydrocarbon residues of 1 to 20 carbons; alkyl of 2 to 6 carbons are preferred.

Recovery of the R-carboxylate enantiomer in optically purified form is thereafter possible permitting its use as an intermediate in the production of pharmaceutical compounds having an absolute R-configuration. Likewise, isolation of the hydrolyzed S-enantiomer followed by esterification provides the oppositely configured S-ester. Finally, racemization of either isolated ester can be performed.

In accordance with the present invention, a method is therefore provided for resolving a mixture of enantiomers, usually a racemic mixture of alkyl 1,4-benzodioxan-2-carboxylates, said method comprising the steps of:

(a) providing an organic phase comprising a mixture of alkyl 1,4-benzodioxan-2-carboxylate enantiomers represented by formula (I)

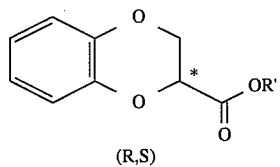

wherein R' is an alkyl group;

(b) contacting said organic phase with an aqueous solution comprising water and a catalytic amount of a microbial esterase derived from *Serratia marcescens* to form a mixture comprising said alkyl (R)-1,4-benzodioxan-2-carboxylate and (S)-1,4-benzodioxan- 2-carboxylic acid;

(c) separating said (S)-1,4-benzodioxan-2-carboxylic acid from said alkyl (R)-1,4-benzodioxan 2-carboxylate; and (d) isolating said (S)-1,4-benzodioxan-2-carboxylic acid.

Steps (a) and (b) are depicted as follows:

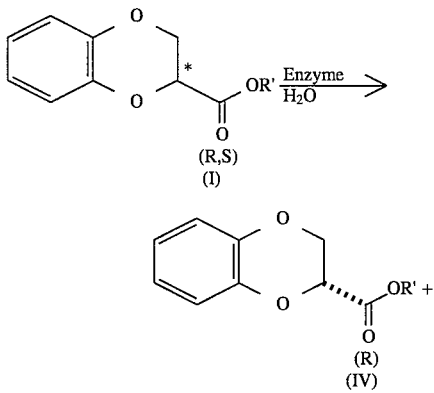

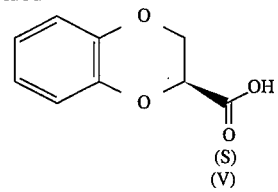

The S-configured carboxylic acid enantiomer represented as formula (V) above can then be esterified to form an optically pure alkyl (S)-1,4-benzodioxan- 2-carboxylate. The alkyl (R)-1,4-benzodioxan- 2-carboxylate enantiomer represented as formula (IV) above remains substantially unaffected by the hydrolysis and can be isolated from the organic solution as the oppositely configured, optically pure alkyl (R)-1,4-benzodioxan-2-carboxylate (IV).

The esterase derived from *Serratia marcescens* is water soluble, whereas the esters of the present invention exhibit very low solubilities in water. Therefore, the enzyme-mediated optical resolution may be conducted under two-phase or multiphase reaction conditions.

In a preferred embodiment, the R' group of formula (I) is an ethyl group, and the racemic mixture comprises ethyl 1,4-benzodioxan-2-carboxylate as shown in formula (III) above. The resolved and isolated (S)-1,4-benzodioxan-2-carboxylic acid can then be used in the synthesis of the S-enantiomer of doxazosin for use as a pharmaceutical. In addition, (S)-1,4-benzodioxan-2-carboxylic acid can be esterified to form ethyl (S)-1,4-benzodioxan-2-carboxylate.

DETAILED DESCRIPTION OF THE INVENTION

The present invention provides a method for the production of resolved alkyl 1,4-benzodioxan-2-carboxylates, subsequently useful as intermediates in the synthesis of optically pure pharmaceutical compounds, such as (S)-doxazosin, for example. Specifically, this invention relates to the production of optically pure pharmaceutical intermediates by enzymatic resolution of racemic alkyl 1,4-benzodioxan-2-carboxylate mixtures (I) using a resolution process in which the racemate is contacted with an esterase derived from *Serratia marcescens*. The alkyl (S)-1,4-benzodioxan-2-carboxylate enantiomer is preferentially hydrolyzed and removed from the R-enantiomer, thus producing enantiomerically enriched alkyl (R)-1,4-benzodioxan- 2-carboxylate (IV) and enantiomerically enriched (S) 1,4-benzodioxan-2-carboxylic acid (V).

The carboxylic acid is easily separated from the remaining R-ester, due to their differential solubilities in organic solvents, by known methods. In the present invention, by virtue of the lipophilicity of alkyl esters, all the benzodioxan esters are soluble in a variety of organic solvents that are immiscible with water, while the enantiomerically enriched (S)-1,4-benzodioxan-2-carboxylic acid product (V) of the hydrolysis is soluble in water at the appropriate pH. (The term "immiscible" as used herein refers to liquids that cannot be uniformly mixed in all proportions, and "immiscible with water" includes solvents which are completely, substantially, or partially immiscible with water—i.e. solvents such as butanol that form a separate organic phase when placed in contact with water.)

The resolution process described herein is a kinetic resolution process in which each enantiomer of the racemic substrate mixture exhibits some susceptibility to enzymatic hydrolysis, but the S-enantiomer is hydrolyzed more rapidly than the R-enantiomer.

The ability of an enzyme to discriminate between two competitively reacting enantiomers may be quantified by the enantioselectivity value E, as described by C. S. Chen et al. (J. Amer. Chem. Soc., 104 (1982) 7294). The formula for calculation of E in the case of a subtractive kinetic resolution process is given as follows:

$$E=\{\ln[(1-x)(1-ee(S))]/\ln[(1-x)(1+ee(S))]\}$$

where x is the degree of conversion of the entire quantity of starting substrate, expressed as a decimal fraction, and ee(S) is the enantiomeric excess of the remaining, non-hydrolyzed substrate enantiomer, also expressed as a decimal fraction. This formula permits comparison of enzyme reactions which have proceeded to different degrees of conversion, in which case direct comparison of the enantiomeric excess of the remaining carboxylic acid ester substrate is not possible. It is also possible to use this E value and corresponding calculations to compare the apparent selectivity of the same enzyme operating under varying conditions.

In the resolution process of the present invention, an infinitely large E value displayed by the enzyme would be ideal. In this case, at 50% hydrolysis of the total starting substrate, 100% of the non-hydrolyzed material will remain in the organic phase after reaction at an optical purity of 100% enantiomeric excess. However, if a given enzyme displays a lower E value, the overall extent of hydrolysis must be allowed to proceed past 50%, to an extent that is determined by the formula derived by Chen et al. and reproduced above. Generally, an E value of at least 25 is necessary for a process to be of commercial value.

Preferably, the enzyme catalyst will be chosen to display the largest E value possible, thus permitting recovery of the greatest amounts of both the non-hydrolyzed alkyl (R)-1,4-benzodioxan-2-carboxylate enantiomer and the hydrolyzed (S)-1,4-benzodioxan- 2-carboxylic acid enantiomer for a given degree of enantiomeric excess. The esterase derived from *Serratia marcescens* has been surprisingly found to be S-selective with a relatively large E value.

Because the racemic alkyl 1,4-benzodioxan-2-carboxylate compound (I) is available at room temperature as a liquid that emulsifies into a second (organic) phase upon addition of an aqueous solution, the racemic mixture may be used in the present invention without addition of an organic solvent. Alternatively, racemic alkyl 1,4-benzodioxan-2-carboxylate (I) may be dissolved in an organic solvent to form an organic phase which is separable from aqueous solution. The selected organic solvent is one which is appreciably immiscible with water, such as hexane, heptane, methyl isobutyl ketone, t-butyl methyl ether, toluene, ethyl acetate, or methylene chloride. However, the invention is not limited to the use of the above-mentioned solvents, and other suitable water immiscible organic solvents that may be used will be obvious to those skilled in the art.

The enzyme catalyst derived from *Serratia marcescens* for use in the present invention may be obtained in aqueous solution. Alternatively, the esterase may be obtained in powdered form and subsequently dissolved in water. While highly purified enzyme preparations are not necessary for the process of this invention, if the enzyme to be used herein has intrinsically low specific activity units (units of catalytic activity per weight of protein), crude preparations thereof can cause practical problems by requiring unnecessarily large volumes of reaction mixtures and correspondingly large reactor volumes.

Sources and cultivation of *Serratia marcescens* information thereof are disclosed in U.S. Pat. No. 5,378,627 to Shibatani et al., U.S. Pat. No. 5,374,554 to Kamatsubara et al., U.S. Pat. No. 5,371,014 to Matsuyama et al., and U.S. Pat. No. 5,393,664 to Kira et al. Microorganisms having IFO numbers assigned thereto, such as *Serratia marcescens* IFO3046, for example, are described in the List of Culture, 8th ed., vol. 1 (1988) published by the Institute for Fermentation, Osaka (IFO) and available therefrom. *Serratia marcescens* ATCC14226 is described in the Catalogue of Bacteria phages rDNA Vectors, 16th ed. (1985) published by American Type Culture Collection (ATCC) and available therefrom.

Briefly, *Serratia marcescens* produces an esterase that may be obtained by extraction from cultured broths of the microorganisms, followed by purifying the extract by a conventional method. In addition, the bacteria may be either wild type or mutants. Recombinant strains derived using genetic means such as cell fusion or genetic engineering may also be used. The medium for cultivating *Serratia marcescens* for use in the present invention may be any medium on which the microorganisms will grow. For example, an ordinary liquid nutrient medium containing carbon sources, nitrogen sources, inorganic salts and organic nutrients can be used.

The concentration of the racemic alkyl 1,4-benzodioxan-2-carboxylate mixture to be hydrolyzed is not critical. Similarly, the concentration of esterase required to effect hydrolysis of the S-carboxylate ester is not critical to the practice of this invention. However, in preferred embodiments, the enzyme concentration will be an amount which is effective to achieve hydrolysis in a reasonable period of time and may depend on the purity of the enzyme.

In the two-phase hydrolysis system, the pH of the aqueous phase may range from about 5.0 to 9.75, which covers the pH optimum for the *Serratia marcescens* preparation in use. It is desirable to maintain the pH of the aqueous phase within the desired range over the course of the hydrolysis by use of a buffer system. Examples of buffers with buffering capacity over the desired range include, but are not limited to, carbonates, bicarbonates, phosphates, borates, and citrates. Additionally, an automatic titrator using NaOH as the titrant, for example, or other pH controlling device may be used.

Similarly, the temperature at which the hydrolysis is performed may vary over a wide range, preferably between about 10°–45° C., provided that both the aqueous and organic phases remain liquid, the enzyme does not experience denaturation at a rate too rapid to allow its use, and the carboxylates remain stable. The relative volumes of the aqueous and organic phases are not critical, and may vary over a wide range. In the preferred embodiments of the present invention, the temperature, the pH of the aqueous phase, the concentration of the enzyme from *Serratia marcescens* in the aqueous phase, and the concentration of the racemic alkyl 1,4-benzodioxan-2-carboxylate compound are chosen such that an optimal combination of rate and enantioselectivity of hydrolysis is realized.

The esterase-catalyzed hydrolysis reaction is conducted by contacting the racemic carboxylate-containing organic phase with the aqueous phase in the presence of the *Serratia marcescens* esterase using conventional stirring or shaking techniques. Alternatively, known methods wherein the enzymatic resolution process is conducted within a multiphase/extractive enzyme membrane reactor may be employed. An example of such a membrane reactor may be found in U.S. Pat. No. 5,077,217 (Matson et al.), the disclosure of which is incorporated by reference.

Since the alkyl 1,4-benzodioxan-2-carboxylate mixture (I) is preferentially soluble in the organic phase and nearly insoluble in the aqueous phase, the R-ester will remain in the organic phase after hydrolysis, and the enantiomeric ester excess (ee Ester) in the organic phase will increase as a function of the extent of hydrolysis and enantioselectivity value E. Likewise, after hydrolysis, the aqueous solution will contain an S-acid and has an enantiomeric acid excess (ee Acid) greater than 0. The extent of hydrolysis of the total racemic alkyl 1,4-benzodioxan-2-carboxylate substrate (I) may be adjusted to permit the recovery of the unreacted R-ester at any desired level of enantiomeric excess; higher conversions yield organic-phase R-esters of increasing optical purity.

The progress of the esterase-catalyzed hydrolysis may be conveniently monitored by periodic HPLC analyses of the reaction mixture until the desired extent of conversion is reached. After completion of the hydrolysis, the optically pure S-acid enantiomer is then separated from the oppositely configured R-carboxylate enantiomer, preferably by separating the aqueous and organic phases. Common methods of separation include, but are not limited to, gravitational settling and centrifugation. Generally, after gravitational settling the aqueous layer can be drained through a tap in the bottom of the reaction vessel.

The substantially optically pure alkyl (R)-1,4-benzodioxan-2-carboxylate (IV) contained in the organic solution may then be isolated by concentrating the organic layer under reduced pressure. Likewise, the (S)-1,4-benzodioxan-2-carboxylic acid (V) produced in the aqueous layer can be isolated by precipitation and filtration, for example, and is therefore available for subsequent use as an intermediate in the syntheses of optically pure pharmaceutical compounds such as S-doxazosin.

In addition, acid catalyzed esterification of the isolated S-carboxylic acid enantiomer may then be performed to obtain the alkyl (S)-1,4-benzodioxan-2-carboxylate enantiomer. Therefore, according to the present invention, both enantiomers, R- and S-, of the racemic alkyl 1,4-benzodioxan-2-carboxylate compound (I) can be resolved and isolated for use as a pharmaceutical precursor.

Racemization of either the isolated R- or S-ester may then be done by refluxing the enantiomer with a base (about 1 mole %) such as potassium-tert-butoxide or sodium-isobutoxide until completion. Alternatively, where the isolated carboxylate enantiomer is a methyl ester, a base such as sodium methoxide may be used, and sodium ethoxide may be used when an ethyl ester enantiomer is being racemized. Refluxing the isolated R- or S- ester with a tertiary amine such as triethylamine or with a strong basic amine such as 1,5-diazabicyclo[4.3.0]non-5-ene or 1,8-diazabicyclo[5.4.0]undec-7-ene will also produce the racemate. Also, refluxing with sodium or potassium hydroxide in catalytic amounts will cause racemization, although with a concomitant loss of ester due to hydroylsis. However, the invention is not limited to refluxing the isolated enantiomer with the aforementioned bases, and other bases that will effect racemization may be used and will be obvious to those skilled in the art. Racemization may be followed by HPLC or by optical rotation to determine the extent of racemization. After the R-carboxylate has been racemized, for example, the enzymatic hydrolysis of the present invention may then be repeated to obtain additional optically pure (S)-1,4-benzodioxan-2-carboxylic acid for use in the synthesis of S-doxazosin.

The present invention is more particularly described and explained by means of the following detailed Examples of preferred embodiments. It is to be understood, however, that such Examples are for illustration purposes only and are not intended to limit the scope of the present invention.

EXAMPLE 1

An organic solution was formed containing 24.8 g of a racemic mixture of ethyl 1,4-benzodioxan-2-carboxylate enantiomers dissolved in 50 mL hexane and 25 mL toluene. The esterase derived from *Serratia marcescens* was obtained from Tanabe Seiyaku Co., Ltd. in an aqueous solution having an enzymatic activity of 5200 units/mL. 0.5 mL of the esterase solution was added to 150 mL of a 0.1M sodium phosphate buffered aqueous solution. The pH was maintained at 8.25 by an automatic titrator using a 2.5M NaOH solution as the titrant. The organic and aqueous solutions were vigorously stirred with a stir plate for 2 hours, and samples were analyzed by HPLC. The reaction was then allowed to phase separate, and the aqueous layer was drained. The organic phase was dried over anhydrous sodium sulfate and evaporated to yield the final product.

Optical purity of the enantiomers was analyzed by HPLC using a Chiralcel™ OD-R column with a 1:1 acetonitrile/buffer as the mobile phase. The buffer was 7 g sodium perchlorate/liter $H_2O$, adjusted to pH of 2.0 with conc. HCl.

The results of the hydrolysis are summarized in the following TABLE.

TABLE

| Time (hr) | eeAcid (%) | eeEster (%) | Conversion (%) | E | Rate (mmol/hr/mlenz) |
| --- | --- | --- | --- | --- | --- |
| 2 | 98.46 | 70.50 | 41.73 | 273 | 58.37 |

The aqueous phase of the hydrolysis reaction was acidified to pH of 2.0 with conc. HCl forming a white precipitate of (S)-1,4-benzodioxan-2-carboxylic acid. The S-acid was filtered and extracted into toluene, and the phases were separated. The organic layer was placed in a vessel suitable for acid catalyzed esterification. Sulfuric acid was added to the vessel, and the mixture was heated to reflux. Water was removed by azeotropic distillation. The conversion of the acid was followed by GC analysis. Ethyl (S)-1,4-benzodioxan-2-carboxylate was thereby formed. Upon completion of the esterification, the sulfuric acid catalyst used in the reaction was removed by washing the reaction product with saturated sodium carbonate, and the S-carboxylate product was azeotropically dried again.

A solution of ethyl (R)-1,4-benzodioxan-2-carboxylate in toluene was racemized by placing the R-carboxylate in a vessel suitable for refluxing and adding potassium-tert-butoxide (about 1 mole %). The solution was refluxed, and the racemization reaction was followed by HPLC analysis. When the reaction was complete, the solution was cooled to room temperature and washed with dilute sodium carbonate. Toluene and water were removed from the solution by distillation leaving the racemic ethyl (R, S)-1,4-benzodioxan-carboxylate behind. The product was confirmed by HPLC and GC analyses.

EXAMPLE 2

Large-scale enzymatic hydrolysis of racemic ethyl 1,4-benzodioxan-2-carboxylate is carried out in three batches in a 200 gallon reactor to produce 100 kg of the unhydrolyzed R-ester enantiomer. Each batch utilizes 67 kg substrate dissolved in 135 liters of heptane or toluene. The aqueous phase comprises 1.67 liters of an enzyme solution derived from *Serratia marcescens* (Tanabe) in 420 liters of a 0.1M sodium phosphate buffer solution adjusted to a pH of 8.25 with 28.6 liters of 5M NaOH. The total volume of the reactants is 651.1 liters such that the reactor is running at 81.3% of its volume capacity.

After completion of hydrolysis, approximately 6 hours, the phases are permitted to separate, and the aqueous layer is drained through a bottom tap. The organic phase is then dried over anhydrous sodium sulfate (about 3 kg for 150 liters) and evaporated to yield ethyl (R)-1,4-benzodioxan-2-carboxylate enantiomer. The (S)-1,4-benzodioxan-2-carboxylic acid is recovered from the aqueous layer by acidification with concentrated HCl followed by filtration of the solid acid. Optical and chemical analyses of the isolated enantiomer may be performed using the chromatographic techniques and conditions listed in EXAMPLE 1.

We claim:

1. A method for resolving a mixture of enantiomers of an alkyl 1,4-benzodioxan-2-carboxylate, said method comprising the steps of:

a) providing an organic phase comprising a mixture of alkyl 1,4-benzodioxan-2-carboxylate enantiomers represented by formula (I)

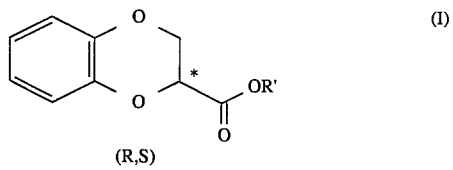

(R,S)

(I)

wherein R' is an alkyl group and * indicates a chiral carbon;

b) contacting said organic phase with an aqueous solution comprising water and a catalytic amount of a microbial esterase obtained from *Serratia marcescens* to form a mixture comprising alkyl (R)-1,4-benzodioxan- 2-carboxylate and (S)-1,4-benzodioxan-2-carboxylic acid;

c) separating said (S)-1,4-benzodioxan-2-carboxylic acid from said alkyl (R)-1,4-benzodioxan 2-carboxylate; and d) isolating said (S)-1,4-benzodioxan-2-carboxylic acid.

2. The method according to claim 1, wherein said organic phase further comprises a water immiscible organic solvent.

3. The method according to claim 1, wherein R' is an ethyl group.

4. The method according to claim 1, wherein said aqueous solution is maintained at a pH in the range of about 5.0 to 9.75.

5. The method according to claim 1, wherein hydrolysis occurs at a temperature from about 10° C. to about 45° C.

6. The method according to claim 1 further comprising the step of recovering said alkyl (R)-1,4-benzodioxan- 2-carboxylate.

7. The method according to claim 1 further comprising the step of esterifying said isolated (S) 1,4-benzodioxan-2-carboxylic acid to produce alkyl (S)-1,4-benzodioxan-2-carboxylate.

8. The method according to claim 1 further comprising the steps of:

recovering said alkyl (R)-1,4-benzodioxan-2-carboxylate from step c); and refluxing said recovered alkyl (R)-1,4-benzodioxan-2-carboxylate with a base to produce a mixture of alkyl (R,S)-1,4-benzodioxan-2-carboxylate enantiomers.

9. The method according to claim 8, wherein said base is selected from the group consisting of potassium-tert-butoxide, potassium hydroxide, sodium hydroxide, sodium methoxide, sodium ethoxide, sodium-iso-butoxide, triethylamine, 1,5-diazabicyclo[4.3.0]non-5-ene, and 1,8-diazabicyclo[5.4.0]undec-7-ene.

10. The method according to claim 1 further comprising the steps of:

esterifying said isolated (S)-1,4-benzodioxan-2-carboxylic acid to produce alkyl (S)-1,4-benzodioxan-2-carboxylate; and refluxing said alkyl (S)-1,4-benzodioxan-2-carboxylate with a base to produce a mixture of alkyl (R,S)-1,4-benzodioxan- 2-carboxylate enantiomers.

11. The method according to claim 10, wherein said base is selected from the group consisting of potassium-tert-butoxide, potassium hydroxide, sodium hydroxide, sodium methoxide, sodium ethoxide, sodium-iso-butoxide, triethylamine, 1,5-diazabicyclo[4.3.0]non-5-ene, and 1,8-diazabicyclo[5.4.0]undec-7-ene.

* * * * *